(12) United States Patent
Besaw et al.

(10) Patent No.: US 11,273,047 B2
(45) Date of Patent: Mar. 15, 2022

(54) EXPANDABLE IMPLANT DEVICE

(71) Applicant: NuVasive, Inc., San Diego, CA (US)

(72) Inventors: Christopher Besaw, San Diego, CA (US); Thomas Sweeney, III, San Diego, CA (US)

(73) Assignee: NUVASIVE, INC., San Diego, CA (US)

( * ) Notice: Subject to any disclaimer, the term of this patent is extended or adjusted under 35 U.S.C. 154(b) by 0 days.

(21) Appl. No.: 16/224,582

(22) Filed: Dec. 18, 2018

(65) Prior Publication Data

US 2019/0201210 A1    Jul. 4, 2019

Related U.S. Application Data

(60) Provisional application No. 62/607,303, filed on Dec. 18, 2017.

(51) Int. Cl.
*A61F 2/44* (2006.01)
*A61F 2/30* (2006.01)
*A61F 2/46* (2006.01)

(52) U.S. Cl.
CPC ............ *A61F 2/4425* (2013.01); *A61F 2/442* (2013.01); *A61F 2/447* (2013.01); *A61F 2/4455* (2013.01); *A61F 2/4611* (2013.01); *A61F 2002/30261* (2013.01); *A61F 2002/30266* (2013.01); *A61F 2002/30329* (2013.01); *A61F 2002/30331* (2013.01); *A61F 2002/30365* (2013.01); *A61F 2002/30405* (2013.01); *A61F 2002/30411* (2013.01); *A61F 2002/30471* (2013.01); *A61F 2002/30507* (2013.01); *A61F 2002/30517* (2013.01); *A61F 2002/30537* (2013.01); *A61F 2002/30538* (2013.01); *A61F 2002/30556* (2013.01); *A61F 2002/30565* (2013.01); *A61F 2002/30576* (2013.01); *A61F 2002/30578* (2013.01); *A61F 2002/30593* (2013.01);
(Continued)

(58) Field of Classification Search
CPC ........... A61F 2/44; A61F 2/447; A61F 2/4425
See application file for complete search history.

(56) References Cited

U.S. PATENT DOCUMENTS

| 5,171,278 A | 12/1992 | Pisharodi |
| 5,390,683 A | 2/1995 | Pisharodi |
| 5,693,100 A | 12/1997 | Pisharodi |

(Continued)

FOREIGN PATENT DOCUMENTS

| AU | 2007202404 | 9/2016 |
| AU | 2011203582 | 9/2016 |

(Continued)

OTHER PUBLICATIONS

International Search Report and Written Opinion, International Application No. PCT/US2018/066297, dated Apr. 1, 2019.

*Primary Examiner* — Christopher J Beccia
(74) *Attorney, Agent, or Firm* — Hoffman Warnick LLC

(57) ABSTRACT

Expandable implant devices including first and second endplates, wherein a first side of the first endplate is moveably attached to a first side of the second endplate; and an expansion mechanism is disposed between the first and second endplates adjacent the second side of the endplates opposite the first side, wherein actuating the expansion mechanism changes an angle between the first endplate and the second endplate.

15 Claims, 12 Drawing Sheets

(52) U.S. Cl.
CPC ............... *A61F 2002/30784* (2013.01); *A61F 2002/443* (2013.01)

(56) References Cited

U.S. PATENT DOCUMENTS

| | | | |
|---|---|---|---|
| 5,782,832 A | 7/1998 | Larsen et al. | |
| 6,126,689 A | 10/2000 | Brett | |
| 6,174,334 B1 | 1/2001 | Suddaby | |
| 6,183,517 B1 | 2/2001 | Suddaby | |
| 6,332,895 B1 | 12/2001 | Suddaby | |
| 6,340,369 B1 | 1/2002 | Ferree | |
| 6,344,058 B1 | 2/2002 | Ferree | |
| 6,352,557 B1 | 3/2002 | Ferree | |
| 6,368,351 B1 | 4/2002 | Glenn | |
| 6,409,766 B1 | 6/2002 | Brett | |
| 6,419,702 B1 | 7/2002 | Ferree | |
| 6,488,710 B2 | 12/2002 | Besselink | |
| 6,491,724 B1 | 12/2002 | Ferree | |
| 6,500,205 B1 | 12/2002 | Michelson | |
| 6,582,451 B1 | 6/2003 | Marucci et al. | |
| 6,648,918 B2 | 11/2003 | Ferree | |
| 6,652,584 B2 | 11/2003 | Michelson | |
| 6,709,458 B2 | 3/2004 | Michelson | |
| 6,716,247 B2 | 4/2004 | Michelson | |
| 6,719,797 B1 | 4/2004 | Ferree | |
| 6,743,255 B2 | 6/2004 | Ferree | |
| 6,793,679 B2 | 9/2004 | Michelson | |
| 6,808,537 B2 | 10/2004 | Michelson | |
| 6,814,756 B1 | 11/2004 | Michelson | |
| 6,962,606 B2 | 11/2005 | Michelson | |
| 6,972,035 B2 | 12/2005 | Michelson | |
| 6,986,772 B2 | 1/2006 | Michelson | |
| 7,008,453 B1 | 3/2006 | Michelson | |
| 7,044,971 B2 | 5/2006 | Suddaby | |
| 7,070,598 B2 | 7/2006 | Lim et al. | |
| 7,083,650 B2 | 8/2006 | Moskowitz et al. | |
| 7,087,055 B2 | 8/2006 | Lim et al. | |
| 7,118,579 B2 | 10/2006 | Michelson | |
| 7,118,598 B2 | 10/2006 | Michelson | |
| 7,547,325 B2 | 6/2009 | Biedermann et al. | |
| 7,608,107 B2 | 10/2009 | Michelson | |
| 7,615,052 B2 | 11/2009 | Serbousek | |
| 7,621,951 B2 | 11/2009 | Glenn et al. | |
| 7,625,377 B2 | 12/2009 | Veldhuizen et al. | |
| 7,655,027 B2 | 2/2010 | Michelson | |
| 7,678,148 B2 | 3/2010 | Peterman | |
| 7,682,400 B2 | 3/2010 | Zwirkoski | |
| 7,763,028 B2 | 7/2010 | Lim et al. | |
| 7,763,074 B2 | 7/2010 | Altarac et al. | |
| 7,846,206 B2 | 12/2010 | Oglaza et al. | |
| 7,892,286 B2 | 2/2011 | Michelson | |
| 7,901,409 B2 | 3/2011 | Canaveral et al. | |
| 7,922,729 B2 | 4/2011 | Michelson | |
| 8,007,534 B2 | 8/2011 | Michelson | |
| 8,025,665 B2 | 9/2011 | Lim et al. | |
| 8,075,621 B2 | 12/2011 | Michelson | |
| 8,097,034 B2 | 1/2012 | Michelson | |
| 8,097,035 B2 | 1/2012 | Glenn et al. | |
| 8,128,662 B2 | 3/2012 | Altarac et al. | |
| 8,152,837 B2 | 4/2012 | Altarac et al. | |
| 8,182,538 B2 | 5/2012 | O'Neil et al. | |
| 8,251,891 B2 | 8/2012 | Moskowitz et al. | |
| 8,268,001 B2 | 9/2012 | Butler et al. | |
| 8,303,658 B2 | 11/2012 | Peterman | |
| 8,303,663 B2 * | 11/2012 | Jimenez ............ F16H 25/2056 623/17.16 | |
| 8,317,798 B2 | 11/2012 | Lim et al. | |
| 8,328,818 B1 | 12/2012 | Seifert et al. | |
| 8,377,071 B2 | 2/2013 | Lim et al. | |
| 8,409,282 B2 | 4/2013 | Kim | |
| 8,444,692 B2 | 5/2013 | Michelson | |
| 8,496,664 B2 | 7/2013 | Michelson | |
| 8,523,944 B2 | 9/2013 | Jimenez et al. | |
| 8,540,452 B2 | 9/2013 | Jimenez et al. | |
| 8,551,173 B2 | 10/2013 | Lechmann et al. | |
| 8,579,907 B2 | 11/2013 | Lim et al. | |
| 8,603,173 B2 | 12/2013 | Biedermann et al. | |
| 8,628,577 B1 | 1/2014 | Jimenez | |
| 8,663,329 B2 | 3/2014 | Ernst | |
| 8,685,095 B2 | 4/2014 | Miller et al. | |
| 8,690,917 B2 | 4/2014 | Suh et al. | |
| 8,734,520 B2 | 5/2014 | Zwirkoski | |
| 8,771,321 B2 | 7/2014 | Michelson | |
| 8,771,358 B2 | 7/2014 | Michelson | |
| 8,795,365 B2 | 8/2014 | Arcenio et al. | |
| 8,795,374 B2 | 8/2014 | Chee | |
| 8,828,085 B1 | 9/2014 | Jensen | |
| 8,845,726 B2 | 9/2014 | Tebbe et al. | |
| 8,845,730 B2 | 9/2014 | de Villiers et al. | |
| 8,894,652 B2 | 11/2014 | Seifert et al. | |
| 8,906,100 B2 | 12/2014 | Jimenez et al. | |
| 8,940,049 B1 | 1/2015 | Jimenez et al. | |
| 8,986,386 B2 | 3/2015 | Oglaza et al. | |
| 8,998,992 B2 | 4/2015 | Seifert et al. | |
| 9,005,291 B2 | 4/2015 | Loebl et al. | |
| 9,034,040 B2 | 5/2015 | Seifert et al. | |
| 9,039,742 B2 | 5/2015 | Altarac et al. | |
| 9,119,726 B2 | 9/2015 | Wei | |
| 9,125,692 B2 | 9/2015 | Kim | |
| 9,138,327 B1 | 9/2015 | McClellan, III | |
| 9,155,572 B2 | 10/2015 | Altarac et al. | |
| 9,204,973 B2 | 12/2015 | Aflatoon et al. | |
| 9,220,535 B2 | 12/2015 | Robling et al. | |
| 9,259,328 B2 | 2/2016 | Pabst et al. | |
| 9,289,308 B2 | 3/2016 | Marino et al. | |
| 9,295,562 B2 | 3/2016 | Lechmann et al. | |
| 9,333,093 B2 | 5/2016 | Aflatoon | |
| 9,345,584 B2 | 5/2016 | Michelson | |
| 9,351,846 B2 | 5/2016 | De Villiers et al. | |
| 9,351,851 B2 | 5/2016 | Huffmaster et al. | |
| 9,381,092 B2 | 7/2016 | Jimenez et al. | |
| 9,393,130 B2 | 7/2016 | Suddaby et al. | |
| 9,408,707 B2 | 8/2016 | Oglaza et al. | |
| 9,408,721 B2 | 8/2016 | Eastlack et al. | |
| 9,414,933 B2 | 8/2016 | Banouskou | |
| 9,421,111 B2 | 8/2016 | Baynham | |
| 9,433,510 B2 | 9/2016 | Lechmann et al. | |
| 9,445,856 B2 | 9/2016 | Seifert et al. | |
| 9,445,917 B2 | 9/2016 | Jimenez et al. | |
| 9,463,099 B2 | 10/2016 | Levy et al. | |
| 9,750,618 B1 | 9/2017 | Daffinson et al. | |
| 2003/0236520 A1 | 12/2003 | Lim et al. | |
| 2005/0080422 A1 | 4/2005 | Otte et al. | |
| 2005/0278036 A1 | 12/2005 | Leonard et al. | |
| 2006/0004455 A1 | 1/2006 | Leonard et al. | |
| 2007/0118222 A1 | 5/2007 | Lang | |
| 2007/0149978 A1 | 6/2007 | Shezifi et al. | |
| 2007/0282443 A1 | 12/2007 | Globerman et al. | |
| 2008/0114367 A1 | 5/2008 | Meyer | |
| 2009/0076607 A1 | 3/2009 | Aalsma et al. | |
| 2009/0157084 A1 | 6/2009 | Aalsma et al. | |
| 2009/0281628 A1 | 11/2009 | Oglaza et al. | |
| 2010/0137862 A1 | 6/2010 | Diao et al. | |
| 2010/0137987 A1 | 6/2010 | Diao et al. | |
| 2010/0217335 A1 | 8/2010 | Chirico et al. | |
| 2011/0029086 A1 | 2/2011 | Glazer et al. | |
| 2011/0257748 A1 | 10/2011 | Liu | |
| 2012/0101530 A1 | 4/2012 | Robling et al. | |
| 2012/0290094 A1 | 11/2012 | Lim et al. | |
| 2013/0103154 A1 | 4/2013 | Trieu et al. | |
| 2013/0116791 A1 | 5/2013 | Theofilos | |
| 2013/0144388 A1 | 6/2013 | Emery et al. | |
| 2013/0190876 A1 | 7/2013 | Drochner et al. | |
| 2013/0297029 A1 | 11/2013 | Kana et al. | |
| 2013/0304213 A1 | 11/2013 | Aflatoon et al. | |
| 2014/0018922 A1 | 1/2014 | Marino et al. | |
| 2014/0031940 A1 | 1/2014 | Banouskou | |
| 2014/0039625 A1 | 2/2014 | To et al. | |
| 2014/0114420 A1 | 4/2014 | Robinson | |
| 2014/0135776 A1 | 5/2014 | Huffmaster et al. | |
| 2014/0148904 A1 | 5/2014 | Robinson | |
| 2014/0156007 A1 | 6/2014 | Pabst et al. | |
| 2014/0163682 A1 | 6/2014 | Iott et al. | |

(56) References Cited

U.S. PATENT DOCUMENTS

| | | | |
|---|---|---|---|
| 2014/0163683 A1* | 6/2014 | Seifert | A61F 2/4425 623/17.15 |
| 2014/0180419 A1 | 6/2014 | Dmuschewsky | |
| 2014/0236296 A1 | 8/2014 | Wagner et al. | |
| 2014/0243983 A1 | 8/2014 | Galea et al. | |
| 2014/0277139 A1 | 9/2014 | Vrionis et al. | |
| 2014/0277492 A1 | 9/2014 | Wei | |
| 2014/0277498 A1 | 9/2014 | Ainsworth et al. | |
| 2014/0277499 A1 | 9/2014 | Ainsworth et al. | |
| 2014/0277508 A1 | 9/2014 | Baynham | |
| 2014/0296984 A1 | 10/2014 | Etminan | |
| 2014/0309741 A1 | 10/2014 | Ganter et al. | |
| 2014/0343677 A1 | 11/2014 | Davis et al. | |
| 2014/0343678 A1 | 11/2014 | Suddaby et al. | |
| 2014/0358246 A1 | 12/2014 | Levy et al. | |
| 2014/0364951 A1 | 12/2014 | De Villiers et al. | |
| 2015/0012098 A1 | 1/2015 | Eastlack et al. | |
| 2015/0112437 A1 | 4/2015 | Davis et al. | |
| 2015/0182347 A1 | 7/2015 | Robinson | |
| 2015/0230935 A1 | 8/2015 | Aflatoon | |
| 2015/0238230 A1 | 8/2015 | Suh et al. | |
| 2015/0342586 A1 | 12/2015 | Lim et al. | |
| 2015/0374507 A1 | 12/2015 | Wolters et al. | |
| 2016/0022434 A1 | 1/2016 | Robinson | |
| 2016/0022438 A1 | 1/2016 | Lamborne et al. | |
| 2016/0030190 A1 | 2/2016 | Robinson | |
| 2016/0067056 A1 | 3/2016 | Armstrong et al. | |
| 2016/0074174 A1 | 3/2016 | Halverson et al. | |
| 2016/0081724 A1 | 3/2016 | Robling et al. | |
| 2016/0089247 A1 | 3/2016 | Nichols et al. | |
| 2016/0242927 A1 | 8/2016 | Seifert et al. | |
| 2016/0250034 A1 | 9/2016 | Loebl et al. | |
| 2016/0256148 A1 | 9/2016 | Huffmaster et al. | |
| 2017/0100255 A1 | 4/2017 | Hleihil et al. | |
| 2017/0304071 A1* | 10/2017 | Black | A61F 2/4455 |
| 2018/0303621 A1* | 10/2018 | Brotman | A61F 2/4455 |

FOREIGN PATENT DOCUMENTS

| | | |
|---|---|---|
| CN | 101502436 | 9/2016 |
| CN | 104248465 | 9/2016 |
| CN | 105232191 | 9/2016 |
| CN | 202568534 | 9/2016 |
| CN | 203183090 | 9/2016 |
| CN | 204306881 | 9/2016 |
| CN | 204931904 | 9/2016 |
| DE | 20314708 | 11/2003 |
| DE | 10344019 | 9/2016 |
| EP | 2777633 | 11/2003 |
| FR | 2717068 | 11/2003 |
| FR | 2813519 | 11/2003 |
| FR | 3006169 | 11/2003 |
| JP | 2008054710 | 11/2003 |
| JP | 2014073405 | 11/2003 |
| JP | 2016013460 | 11/2003 |
| KR | 100395252 | 11/2003 |
| KR | 20020084349 | 11/2003 |
| RU | 2070006 | 11/2003 |
| WO | WO200103616 | 11/2003 |
| WO | WO2005006944 | 11/2003 |
| WO | WO2006042334 | 11/2003 |
| WO | WO2007038349 | 11/2003 |
| WO | WO2007070024 | 11/2003 |
| WO | WO9214423 | 4/2008 |
| WO | WO9525485 | 4/2008 |
| WO | WO2008044057 | 4/2008 |
| WO | WO2010078468 | 4/2008 |
| WO | WO2012089317 | 4/2008 |
| WO | WO2014091028 | 4/2008 |
| WO | WO2014144696 | 4/2008 |
| WO | WO2014186384 | 4/2008 |
| WO | WO2015063719 | 4/2008 |
| WO | WO2015063721 | 4/2008 |
| WO | WO2015097416 | 4/2008 |
| WO | WO2015198335 | 4/2008 |
| WO | WO2016040125 | 4/2008 |
| WO | 2016/183382 A1 | 11/2016 |

* cited by examiner

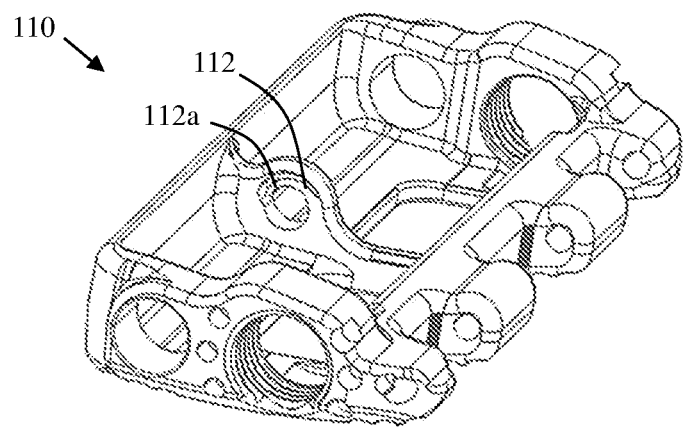
FIG. 11
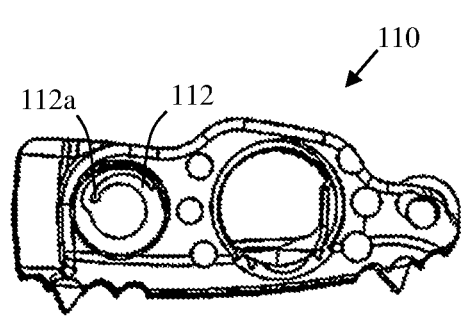 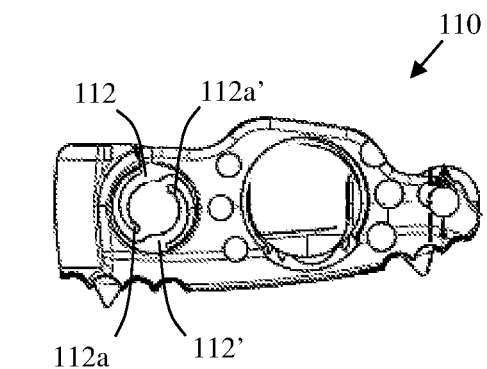
FIG. 12 FIG. 13

EXPANDABLE IMPLANT DEVICE

CROSS REFERENCE TO RELATED APPLICATIONS

This application claims benefit to U.S. Provisional Application No. 62/607,303, filed on Dec. 18, 2017 the entire contents of which are hereby expressly incorporated by reference into this disclosure as if set forth fully herein.

BACKGROUND

Field of the Invention

The present disclosure relates generally to medical implants, and more particularly to expandable medical implants.

Description of the Related Art

Back problems are one of the most common and debilitating occurrences in people of all ethnicities. In the United States alone, over 500,000 spine lumbar and cervical fusion procedures are performed each year. One of the causes of back pain and disability results from the rupture or degeneration of one or more intervertebral discs in the spine.

Surgical procedures are commonly performed to correct problems with displaced, damaged, or degenerated intervertebral discs due to trauma, disease or aging. Generally, spinal fusion procedures involve removing some or all of the diseased or damaged disc, and inserting one or more intervertebral implants into the resulting disc space. Anterior lumbar interbody fusion (ALIF) and lateral lumbar interbody fusion procedures are two of the techniques that spine surgeons use to access the portions of the spine to be repaired or replaced.

Replacement of injured or deteriorated spinal bone with artificial implants requires a balance of knowledge of the mechanisms of the stresses inherent in the spine, as well as the biological properties of the body in response to the devices. Further, the size, configuration, and placement of an artificial implant requires precision positioning and handling by a skilled surgeon.

SUMMARY OF THE INVENTION

This disclosure includes expandable implant devices and methods for using the same. The expandable implant device may be adjusted to form a particular lordosis angle, as influenced by inter alia: the needs of the patient, the requirements of the patient, the target procedure of a surgeon, and may incorporate various features to accommodate spinal fusion.

In some embodiments, an expandable implant device includes: a first endplate having a first side and a second side, and a second endplate having a first side and a second side; wherein a first end of the first endplate is moveably attached to a first end of the first endplate. The expandable implant device further includes an angle actuation mechanism disposed on the first endplate. The angle actuation mechanism may be configured to vary an angle between the second endplate and the first endplate. The expandable implant device may have a first closed configuration, and at least one open configuration conforming the expandable implant device to a chosen angle of lordosis.

In some embodiments, the angle actuation mechanism may include a drive screw rotatably coupled to one of the first endplate or second endplate with at least one threaded nut configured to receive at least a portion of the drive screw, and wherein the at least one threaded nut is configured to translate along a length of the drive screw upon a rotation of the drive screw. Each threaded nut may be coupled to at least one linkage, with each linkages extending from one of the at least one threaded nuts to the second endplate. Upon a rotation of the drive screw the at least one threaded nut translates along a length of the drive screw; and the travel of the at least one threaded nut may impart a movement of the at least one linkage, thereby changing an angle between the first endplate and the second endplate.

An embodiment of a method of use of an expandable implant device is also provided, the method including the steps: accessing an intervertebral disc space of a patient; preparing the disc space to receive an implant; inserting the expandable implant device into a prepared disc space in a closed configuration; rotating a drive screw of the expandable implant device using an expansion tool to actuate the expandable implant device to change an angle between the first endplate and the second endplate.

BRIEF DESCRIPTION OF THE DRAWINGS

These and other features will be further understood by those with skill in the art upon a review of the appended drawings, wherein:

FIG. 11 shows a perspective view of a first endplate of an expandable implant device, wherein the first endplate includes a leaf spring with a spring end configured to engage a spline of a drive screw to prevent undesired rotation of the drive screw;

FIG. 12 shows a side view of the first endplate in accordance with the first embodiment having one leaf spring and a spring end configured to engage a spline of a drive screw to prevent undesired rotation;

FIG. 13 shows an embodiment of a first endplate having two opposing leaf springs and two spring ends configured to engage a spline of a drive screw to further prevent undesired rotation of the drive screw;

DETAILED DESCRIPTION

Figure 1:
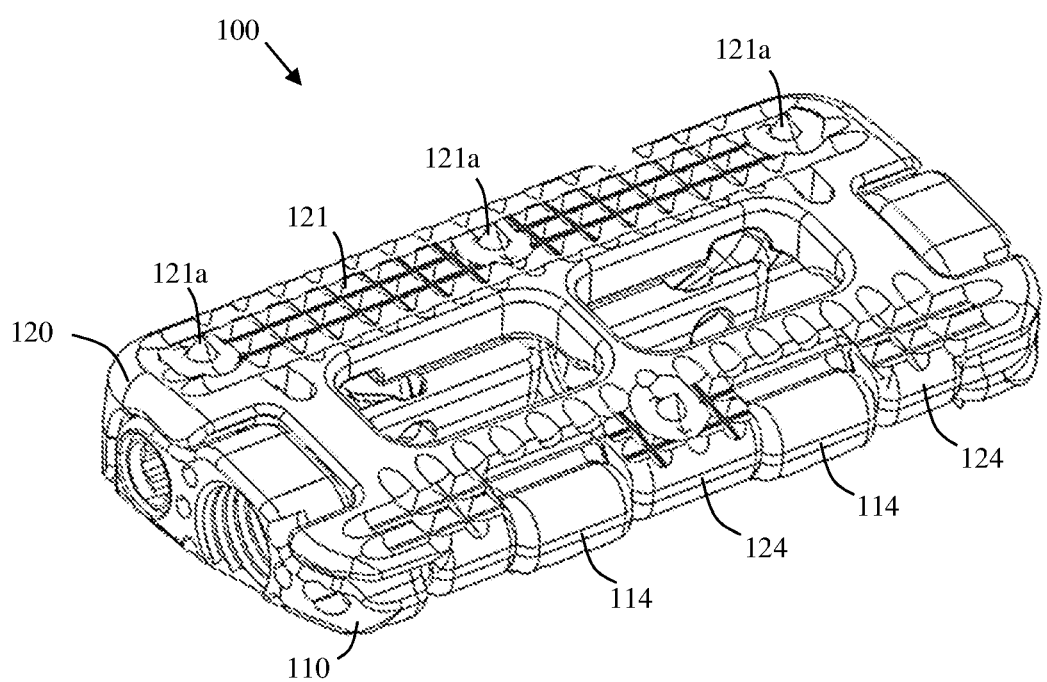
FIG. 1 shows a perspective view of an expandable implant device in accordance with a first embodiment.

For purposes of explanation and not limitation, details and descriptions of certain embodiments and methods are hereinafter provided such that one having ordinary skill in the art may be enabled to make and use the invention. These details and descriptions are representative only of certain embodiments. However, a myriad of other embodiments which will not be expressly described will be readily understood by those having skill in the art upon a thorough review hereof.

In a general embodiment, an expandable implant device includes a first endplate having a leading end, a trailing end, a first side, and a second side, and a second endplate having a leading end, a trailing end, a first side and a second side, wherein a first side of the first endplate is moveably attached to a first side of the second endplate. The implant further includes an expansion mechanism disposed between the first and second endplates. The expansion mechanism may be configured to vary a distance between the first and second endplates.

The expansion mechanism may include a drive screw rotatably coupled to the second endplate. The expansion mechanism includes at least one threaded nut configured to receive at least a portion of the drive screw, and wherein the at least one threaded nut is configured to translate along a length of the drive screw upon a rotation of the drive screw. Each threaded nut is coupled to at least one linkage. The linkage has a first end pivotably coupled to the threaded nut and a second end in contact with an interior surface of the first endplate. Upon a rotation of the drive screw, the at least one threaded nut translates along the length of the drive screw and the travel of the at least one nut pivots the at least one linkage and causes the angle of the linkage relative to the drive screw to change, thereby changing the distance between the first and second endplates. For example, translation of the threaded nut in a first direction pivots the linkage and causes the linkage to become more vertical, i.e. increases the angle between the linkage and the drive screw thereby increasing the distance between the first and second endplates, and translation of the threaded screw in a direction opposite the first direction pivots the linkage and causes the linkage to become more horizontal, i.e. decreases the angle between the linkage and the drive screw thereby decreasing the distance between the first and second endplates. According to an exemplary embodiment, the expansion mechanism further includes a locking mechanism to inhibit undesired or unintentional rotation of the drive screw while the implant is in use.

In some embodiments, the drive screw includes: a first threaded shank portion configured to receive a spline at an end thereof; a second threaded shank portion also configured to receive a spline at an end thereof; and a spline to couple the first threaded shank portion to the second threaded shank portion. In an exemplary embodiment, the threaded pattern of the first threaded shank is opposite the thread pattern of the second threaded shank. For example, the first threaded shank may have a left-handed thread pattern and the second threaded shank may have a right handed thread pattern.

The locking mechanism of the expandable implant device according to an exemplary embodiment may include at least one leaf spring with a spring end, wherein the spring end of the leaf spring is configured to engage the spline of the drive screw to prevent undesired rotation of the drive screw. This restriction of the movement of the drive screw prevents undesired rotation of the drive screw thereby preventing collapse of the expandable implant device after it has been expanded to its desired position.

In use, the surgical procedure may include packing the expandable implant device with bone graft or bone graft substitute before and/or after the device has been positioned within the prepared intervertebral disc space of a patient. According to a general embodiment, the expansion mechanism is positioned adjacent the first or second side of the implant. In one exemplary embodiment, the expansion mechanism resides adjacent the second side of the expandable implant, and the second side of the implant is the anterior side of the implant once positioned with a patient's disc space. Placement of the expansion mechanism adjacent the first or second side of the expandable implant allows grafting material to be placed in the center of the expandable implant device and/or allows for bone growth through the center of the expandable implant, which is advantageous to the fusion process.

In some embodiments, at least one of the first or second endplates further comprise planar extensions extending generally perpendicular to the bone contact surface of the endplate. The planar extensions can be configured to enclose an inner volume of the expandable implant device to contain bone graft or bone graft substitute material within the implant. In this sense, the bone graft or bone graft substitute may be enclosed within side walls of the implant. These side walls may include: proximal sidewalls of the first and second endplates, distal sidewalls of the first and second endplates; anterior or posterior sidewalls of the first and second endplates, the hinge formed between the of the first and second endplates, planar extensions of the first and second endplates; and the interior surfaces of the first endplate and the second endplate.

In some embodiments, each of the first and second endplates may further comprise at least one fusion aperture extending through the endplate from a bone contact surface of the endplate into the inner volume of the expandable implant device. These fusion apertures allow direct contact between the bone graft or bone graft substitute material placed within the volume of the expandable implant device, and the bone of the patient, thereby benefiting the fusion process. According to an exemplary embodiment, the fusion apertures are situated in the endplates such that there is no overlap between the fusion apertures and the expansion mechanism in the implant. For example, the expansion mechanism does not interfere with or invade the interior volume of the expandable implant device located directly between the fusion aperture or apertures in the first endplate and the fusion aperture or apertures in the second endplate.

Various external fixation devices may be incorporated into the design to restrict movement or slippage of the expandable implant device in situ relative to the bone structure of a patient. In some embodiments one or more of the first or second endplates may include an aperture configured to receive at least a portion of a bone fixation device therethrough. Wherein upon inserting at least a portion of the bone fixation device through the aperture, and affixing the bone fixation device to a bone of a patient, the bone fixation device prevents slippage of the expandable implant device relative to the bone.

In some other embodiments an expandable implant device may include a threaded aperture on a side of the expandable implant device. The threaded aperture may be disposed for example at least on one of a proximal or distal end of the expandable implant device, and configured to receive a combiner to secure a plate to the expandable implant device.

Wherein the plate is a fixation plate, the plate may be configured to receive at least a portion of a bone fixation device therethrough. Wherein upon inserting at least a portion of the bone fixation device through the fixation plate, and affixing the bone fixation device to a bone of a patient, the bone fixation device and the fixation plate prevent slippage of the expandable implant device relative to the bone.

As one with skill in the art may appreciate, the bone fixation device can include a bone screw, a cannulated bone screw, a modular bone screw, a hook, or any bone fixation device known and contemplated in the art.

Now, turning to the drawings, FIG. 1 shows a perspective view of an expandable implant device 100 in accordance with a first embodiment. An expandable implant device 100 provides many advantages over a traditional non-expandable interbody cage. For example, an expandable implant device 100 in accordance with this disclosure may allow a surgeon to adjust a relative angle of the implant to provide a custom fit within a patient's intervertebral disc space.

Adjustment of an expandable implant device 100 may alter a relative angle between a first endplate 110 and a second endplate 120. This angle, as it relates to the dimension of the expandable implant device 100 as a whole, may correspond to a lordosis angle in an intervertebral disc space of a patient. However, as one with skill in the art may appreciate, the provided expandable implant device 100 may be used in other fields of orthopedics in addition to spinal surgery.

The expandable implant device 100 of FIG. 1 includes a first endplate 110 and a second endplate 120. Each of the first and second endplates 110, 120 includes at least one bone engagement surface 121 for preventing slippage of the expandable implant device 100 with respect to the bone or intervertebral space of the patient. The bone engagement surface 121 may include dimples, trenches, or other anti-migration features. Alternatively, the bone engagement surface may be formed of a porous surface configured to encourage bone ingrowth and/or on growth to the bone engagement surface of the endplates. The illustrated embodiment includes one or more spikes 121a. The spikes 121a may be distributed at various locations on the bone engagement surface 121 in addition to the anti-migration features and/or porous surface of the bone engagement surfaces 121.

The expandable implant device 100 of FIG. 1 includes a hinge formed between the first endplate 110 and the second endplate 120. According to the exemplary embodiment, the hinge is formed by the mating of one or more knuckle portions 114 of the second endplate 120 with one or more knuckle portions 124 of the first endplate 110. The knuckle portions 114 of the first endplate 110 are moveably coupled to the knuckle portions 124 of the second endplate 120 by a hinge pin 160. In the instant embodiment, the knuckle portions of one or more of the first endplate 110 and the second endplate 120 include a bone engagement surface 121. Extending the bone engagement surface 121 over the hinge may help prevent slippage of the expandable implant device 100 with respect to the bone, or intervertebral space of the patient.

The expandable implant device of FIG. 1 further includes fusion apertures 120a extending through the second endplate 120 from the bone engagement surface to opposite, interior surface of the endplate 120. Accordingly, the first endplate 110 also includes fusion apertures 110a extending through the endplate from the bone engagement surface to an opposite, interior surface of the first endplate 110. While the exemplary embodiment is illustrated as having two fusion apertures in each endplate, it is contemplated that each endplate may have only a single fusion aperture or, alternatively, each endplate may have two or more fusion apertures.

Figure 2:
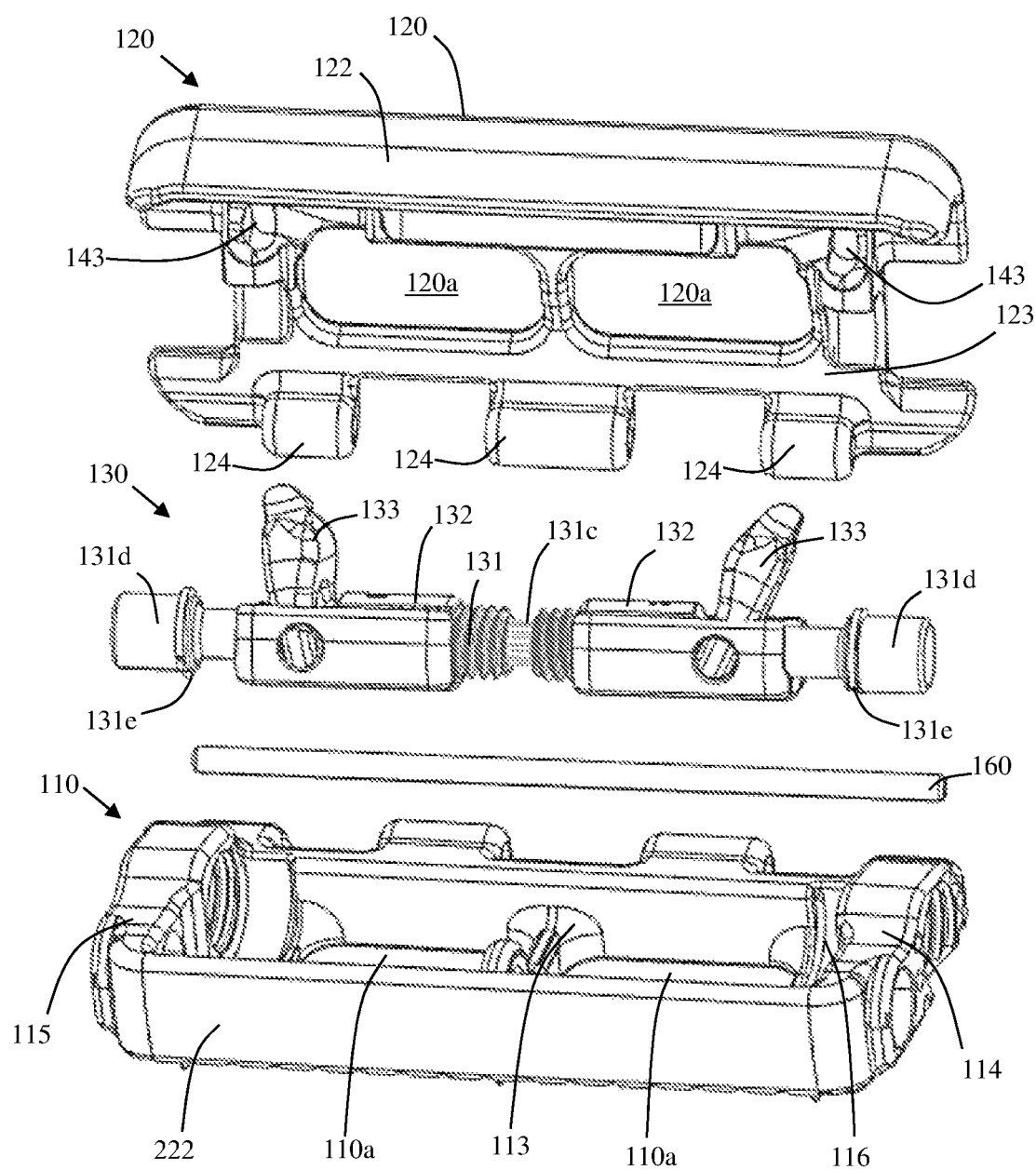
FIG. 2 shows an exploded view of the expandable implant device in accordance with the first embodiment, the expandable implant device shown including a second endplate, an angle actuation mechanism, and an first endplate.

FIG. 2 provides an exploded view of an expandable implant device 100 in accordance with the embodiment of FIG. 1. The first endplate is shown including two fusion apertures 110a, a planar extension 222 extending generally perpendicular to the bone engagement surface of the first endplate, an interior surface 113, a proximal sidewall, a distal sidewall and hinge knuckle portions 114. The second endplate 120 is shown including two fusion apertures 120a, a planar extension 122, an interior surface 123, and hinge knuckle portions 124 to moveably join the second endplate 120 to the first endplate 110 via the hinge pin 160.

As illustrated in the exemplary embodiment, a hinge mating is herein shown comprising complementary hinge knuckle portions 114, 124 moveable about a hinge pin 160. However, it is contemplated that any known method to provide a moveable or hinge connection between the first and second endplates may be provided, including, for example, forming the two endplates from a single unitary piece.

FIG. 2 further illustrates an exemplary expansion mechanism 130 including a drive screw 131 having first and second threaded shank portions, first and second threaded nuts 132, and first and second linkages 133. The drive screw 131 is shown including first and second heads 131d, with each head 131d configured to be disposed on an opposite end of the expandable implant device 100.

Figure 3:
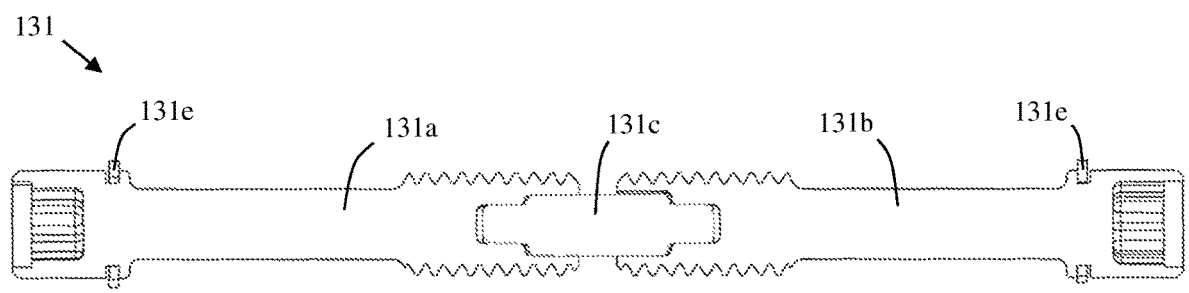
FIG. 3 shows a cross-sectional side view of a drive screw in accordance with the first embodiment.

As illustrated in FIGS. 2 and 3, the drive screw 131 according to the exemplary embodiment of FIG. 1, includes a first threaded shank portion 131a joined to a second threaded shank portion 132b by a spline 131c. The drive screw 131 is shown including one or more retaining clips 131e disposed thereon. According to the illustrated embodiment, when nested within retaining clip grooves 116 disposed on the interior surface of the first endplate 110, the retaining clips 131e will provide resistance to axial movement to keep the drive screw 131 positioned within the expandable implant device 100. The retaining clips 131e may also assist in maintaining the two threaded shank portions 131a, 131b with respect to the spline 131c.

As one with skill in the art will appreciate, the expandable implant device 100 according to the exemplary embodiment is designed such that the implant is symmetric about the central plane bisecting the leading and trailing end. According to the exemplary embodiment this particular plane may be considered to be the sagittal plane in a lateral approach. However, it is alternatively contemplated that this plane may be represented by other anatomical planes for alterative surgical approaches. This feature allows the implant to be inserted to both sides the disc space with either the leading or trailing end. Additionally, as the implant is a mirror image about this central plane, the drive screw and graft packing aperture features are present and able to be actuated from either the leading or trailing end, allowing expansion and bone graft packing from either side upon insertion into the disc space.

Figures 4, 5:
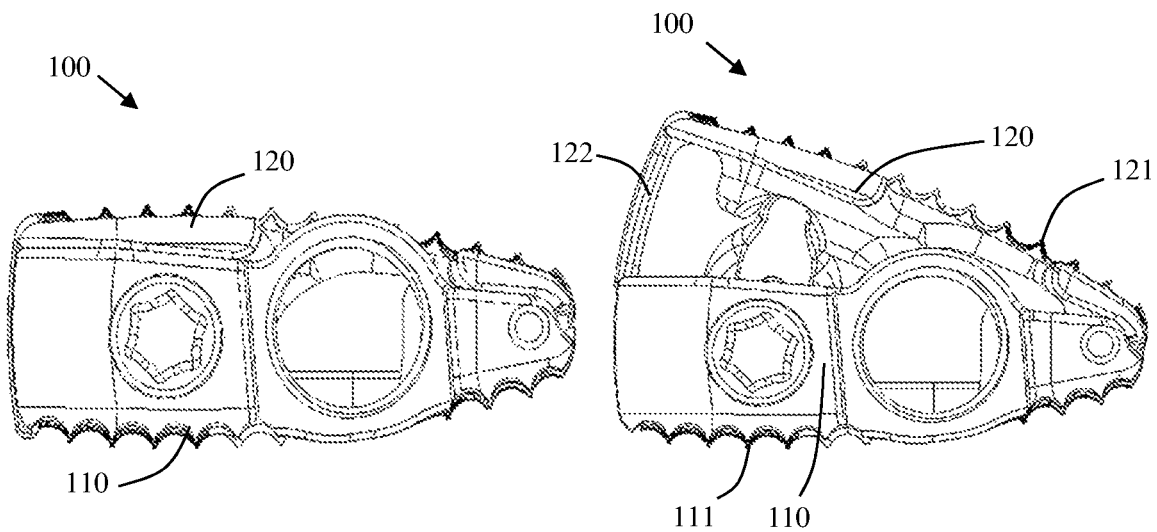
FIG. 4 shows a side view of the expandable implant device in accordance with the first embodiment, the expandable implant device shown in a closed configuration.
FIG. 5 shows a side view of the expandable implant device in accordance with the first embodiment, the expandable implant device shown in an open configuration adjusted to an exemplary lordosis angle.

FIGS. 4-5 show side views of the trailing and/or leading end of the expandable implant device 100 in accordance with the first embodiment. FIG. 4 illustrates the expandable implant device 100 in its collapsed or unexpanded configuration having an initial lordosis angle. According to one exemplary embodiment, the lordosis angle of the implant (i.e. angle between the bone contacting surfaces of the first and second endplates) in its unexpanded state is small. An implant with a small lordosis angle, for example, between 0°-10°, may be beneficial during insertion of an implant into an intervertebral disc space. FIG. 5 illustrates the expandable implant device in an expanded configuration, wherein the lordosis angle is greater than the initial lordosis angle of the unexpanded implant. While the implant in FIGS. 4-5 are shown having a small initial lordosis angle in the unexpanded configuration, it is also contemplated that the implant may have an unexpanded configuration wherein the initial lordosis angle is greater than 10°.

Figure 6:
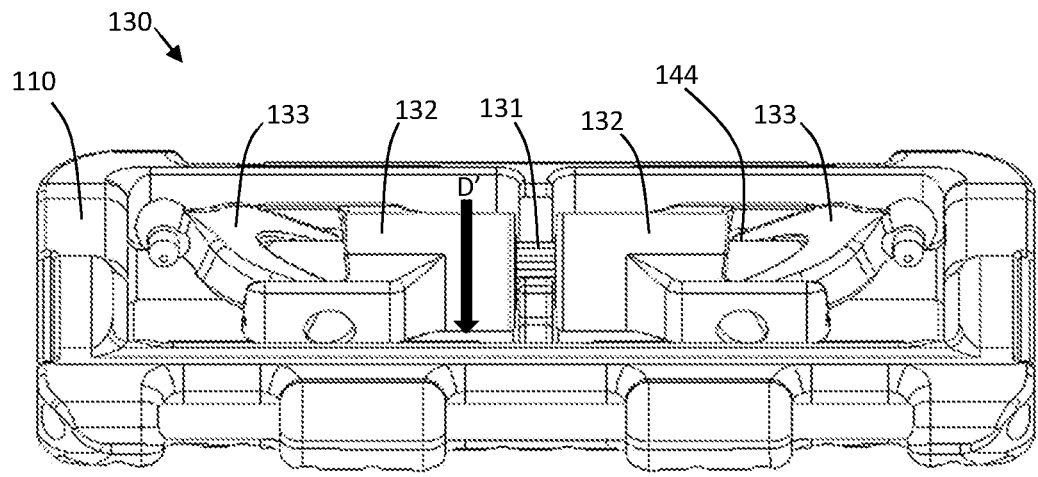
FIG. 6 shows a perspective view of an first endplate in accordance with a second embodiment of an expandable implant, the first endplate having an angle actuation mechanism disposed therein, the angle actuation mechanism shown adjusted in accordance with an open configuration.
Figure 7:
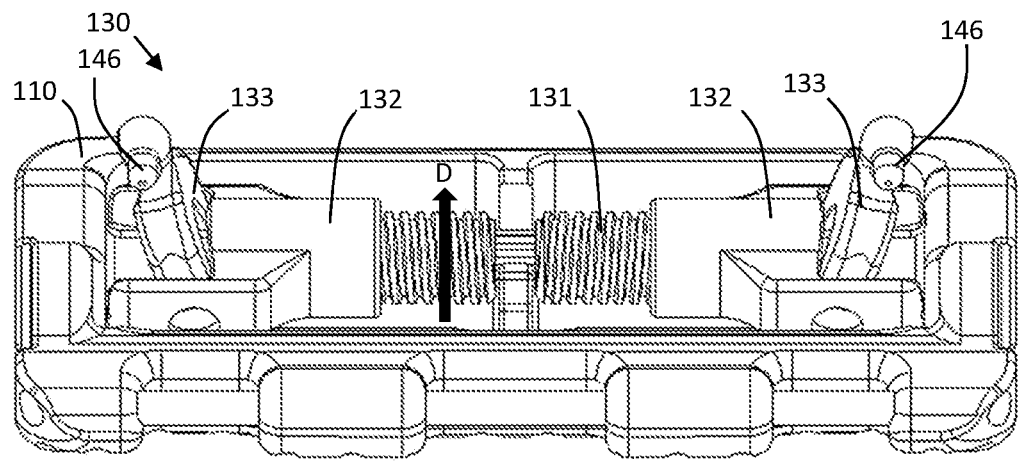
FIG. 7 shows a perspective view of an first endplate in accordance with the second embodiment of an expandable implant, the first endplate having an angle actuation mechanism disposed therein the angle actuation mechanism shown adjusted in accordance with a closed configuration.
Figure 8:
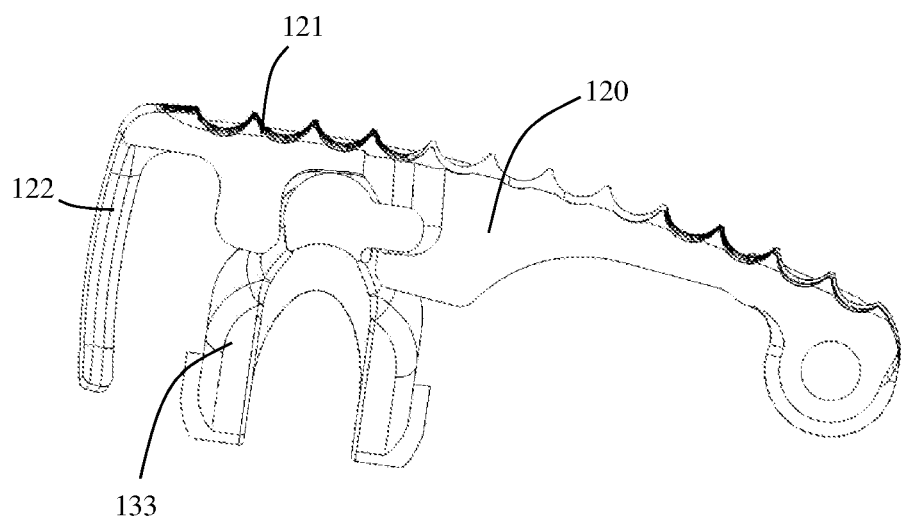
FIG. 8 shows a cross-sectional side view of a linkage movably coupled to a second endplate.
Figure 9:
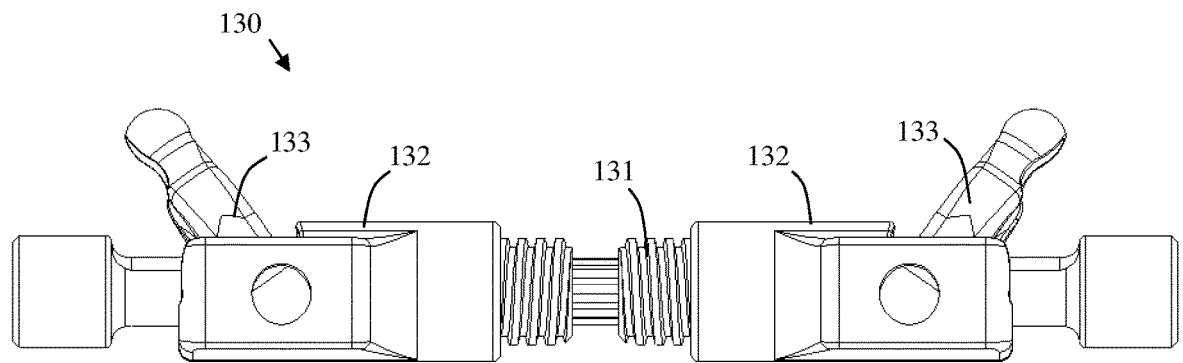
FIG. 9 shows an angle actuation mechanism in accordance with a third embodiment of an expandable implant.

FIGS. 6-7 and FIGS. 9-10 illustrate the mechanical actuation of an expansion mechanism 130 disposed within a first endplate 110 according to an exemplary embodiment. FIG. 6 shows the expansion mechanism 130 in its unexpanded or insertion state. In the unexpanded state, the threaded nuts reside near the center of the implant adjacent the spline 131c, and the linkages 133 are laying down in a generally horizontal position adjacent the shank of the drive screw. Each linkage 133 has a first end 144 pivotably coupled to a threaded nut and a second end 146 configured to pivotably engage with a corresponding pocket 143 on the interior surface 123 of the second endplate 120 (see, for example, the illustration in FIG. 8). During actuation of the expansion mechanism 130, the drive screw 131 is rotated. For example, the drive screw may be rotated by applying torque to a drive screw head 131d with an implant inserter or other driver instrument. Upon rotation of the drive screw 131 the threaded shank portions of the drive screw engage the threads on the respective threaded nuts 132, causing the threaded nuts to translate away from the center of the drive screw 131. As the threaded nuts 132 translate away from the center of the drive screw 131, the linkages pivot about their connection with the threaded nut into a more vertical position, thereby pushing the second endplate 120 away from the first endplate 110 and causing the second endplate 120 to pivot about the hinge pin 160 and increasing the distance between the first side of the first endplate and the first side of the second endplate, and consequently increasing the lordosis angle between the first and second endplates. FIG. 7 shows a perspective view of the same first endplate 110, with the expansion mechanism 130 shown adjusted to its fully expanded state. In the fully expanded state, the threaded nuts 132 are each adjacent the respective leading or trailing end of the implant and the linkages 133 are in a more vertical position than in the unexpanded state.

For example, and as one with skill in the art may appreciate, a rotation of the drive screw 131 of FIG. 6, in a first direction D, may cause the threaded nuts 132 to translate along the drive screw 131 until reaching a maximum point of adjustment at which the threaded nuts would remain at a position similar to FIG. 7. Similarly, a rotation of the drive screw in a second direction D', wherein the second direction D' is opposite the first direction D, may cause the threaded nuts to move to an unexpanded configuration similar that shown in to FIG. 6. Translation of each threaded nut 132 along the drive screw 131 occurs, because each threaded nut 132 is configured to receive at least a portion of the drive screw 131 therein. By coupling each threaded nut 132 to a linkage 133, and in turn coupling each linkage 133 to a second endplate, coaxial rotation of each threaded nut 132 upon the drive screw 131 is prevented. As the drive screw 131 rotates, the interaction of a threaded surface of the drive screw 131 with each complementary threaded surface of each threaded nut 132, provides either a push or pull force (depending on the thread and the direction of rotation of the screw D, D') upon each threaded nut 132, along the length of the screw.

According to an exemplary embodiment, the drive screw 131 may comprise multiple components, for example, a first shank portion and a second shank portion coupled by a spline. However, it is alternatively contemplated that the drive screw may be a single monolithic drive screw. It is further contemplated that the threads of the drive screw may be one continuous thread, or one or more opposing thread patterns.

Figure 10:
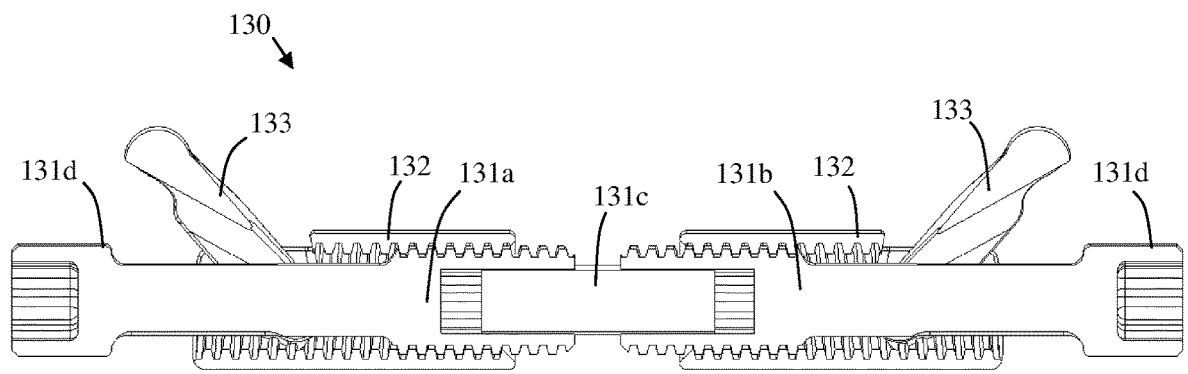
FIG. 10 shows a cross-sectional view of the angle actuation mechanism in accordance with a third embodiment of an expandable implant.

FIG. 10 shows a cross-sectional side view of the expansion mechanism 130, wherein the drive screw 131 includes a first threaded shank portion 131a coupled to a second threaded shank portion 131b by a spline 131c. The spline 131c acts to couple the first threaded shank portion 131b to the second threaded shank portion 131b to form a drive screw 131 and provide an uneven surface which can be utilized to restrict rotation of the drive screw 131 and may help prevent undesired rotation of the drive screw 131 or collapse of the expandable implant device 100.

FIG. 11 shows a perspective view of first endplate 110 including a leaf spring 112 with a spring end 112a configured to engage a spline (FIG. 10, 131c) of a drive screw 131 to prevent undesired rotation of the drive screw 131. This feature provides an added rigidity to the expandable implant, in that the leaf spring 112 provides a resistance to prevent undesired slippage of the drive screw 131 or collapse of the expandable implant device 100 which may be caused by vibration and/or loading of the implant.

The leaf spring 112 may provide a restriction on the direction with which the drive screw 131 may rotate. This restriction prevents undesired slippage of the expandable implant device 100, as may be caused by the compressive forces exerted on the expandable implant device 100 in situ due to excessive loading.

FIG. 12 shows a side view of the first endplate 110 including one leaf spring 112 and a spring end 112a configured to engage a spline of a drive screw to prevent undesired rotation.

In some embodiments, multiple leaf springs are added to provide additional rigidity. FIG. 13 shows an embodiment of a first endplate 110 having two opposing leaf springs (112, 112') and two spring ends (112a, 112a') configured to contemporaneously engage a spline 131c of a drive screw 131 to further prevent undesired rotation of the drive screw 131. Two opposing spring ends 112a engaging the spline 131c of the drive screw 131 may provide additional support to the expandable implant device 100, reinforcing the expandable implant device 100 and helping prevent collapse.

Figure 14:
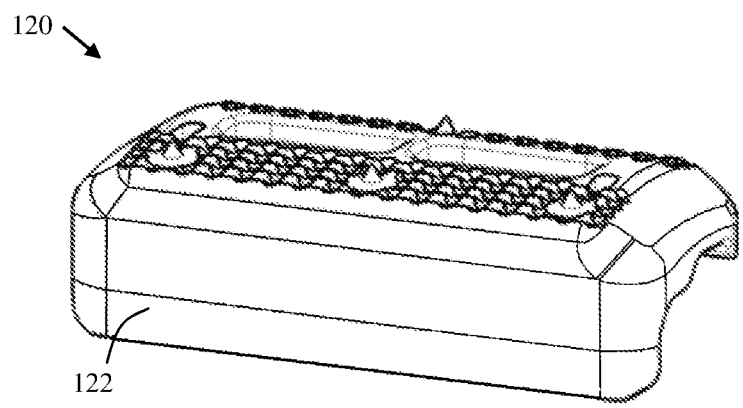
FIG. 14 shows an embodiment of a second endplate with a 10 mm planar extension.
Figure 15:
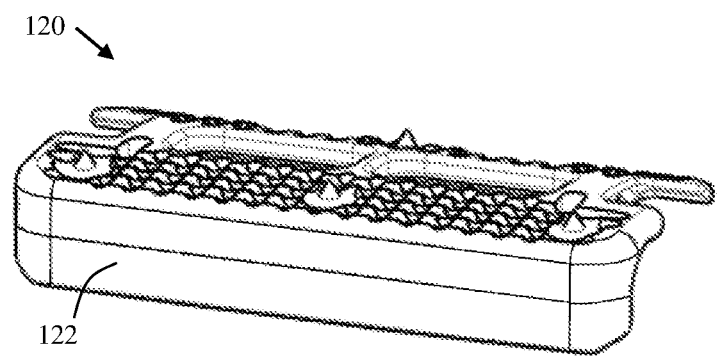
FIG. 15 shows an embodiment of a second endplate with a 4 mm planar extension.

FIG. 14 and FIG. 15 illustrate various embodiments of a second endplate 120 with planar extensions 122 of various lengths. The length of the planar extension 122 may be chosen to complement a target lordosis angle, in order to enclose the relative volume within the expandable implant device 100 between the first endplate 110 and the second endplate 120. This volume may be utilized to pack the implant with bone graft or bone graft substitute either before or after the expandable implant device 100 has been expanded to the desired level of lordosis. The length of the planar extension 122 can be chosen to substantially enclose the inner volume of the expandable implant device 100, which may vary depending on the required lordosis angle. As one with skill in the art may appreciate, any number of other lengths may be provided for the planar extension 122.

Figure 16:
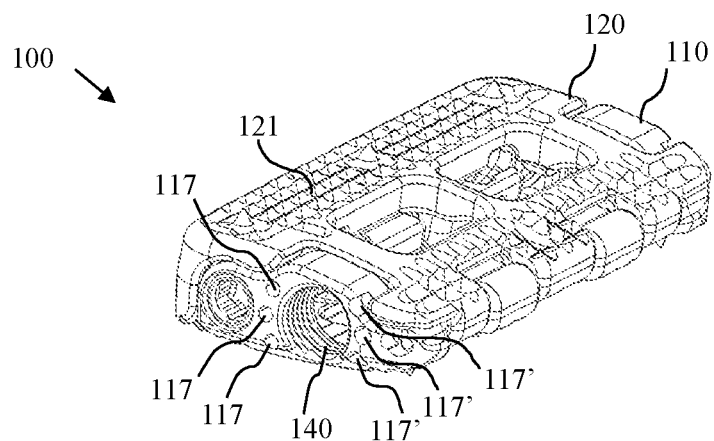
FIG. 16 shows a perspective view of an expandable implant device in accordance with the first embodiment, the expandable implant device having a threaded aperture disposed on a side of the expandable implant device.

FIG. 16 shows a perspective view of an expandable implant device 100 in accordance with the first embodiment, the expandable implant device 100 having a threaded aperture 140 disposed on a proximal end or trailing end thereof. The threaded aperture 140 may be utilized to fill the expandable implant device 100 with bone graft or bone graft substitute for post packing purposes after the expandable implant device 100 has been adjusted to a desired lordosis angle. Upon packing the expandable implant device 100 with bone graft or bone graft substitute, a fixation plate 150 may be coupled to the threaded aperture 140, for example, via a set screw 141.

While the exemplary embodiments illustrate a device having only one expansion mechanism adjacent one side of the implant, an expandable implant device having two expansion mechanisms is also contemplated. For example, an alternative embodiment of the expandable implant device includes a first and second expansion mechanism, with the first expansion mechanism adjacent one side of the expandable implant device, and a second expansion mechanism adjacent the opposite side of the expandable implant device. The expandable implant device according to this alternative embodiment has the second expansion mechanism adjacent the first side of the implant instead of a hinge coupling the first sides of the first and second endplates. According to this exemplary alternative embodiment, the first and second expansion mechanism may be actuated independently, allowing a user to choose to actuate and therefore expand only one side of the expandable implant in order to adjust a lordosis angle, or to actuate both the first and second expansion mechanisms in order to adjust the overall height of the implant adjacent both the first and second sides of the implant. For example, actuating both expansion mechanisms allows the user to perform parallel expansion of the implant, or to fine tune the lordosis angle by adjusting the heights of both the first and second sides of the implant, according to the specific needs of a patient. According to this embodiment, the second expansion mechanism may be structurally identical to the first, and positioned generally parallel to the first implant. Also according this alternative embodiment, both the first and second sides of the first and/or second endplates may include a planar extension for containing bone graft or bone graft substitute within the interior volume of the implant.

Figures 22, 23:
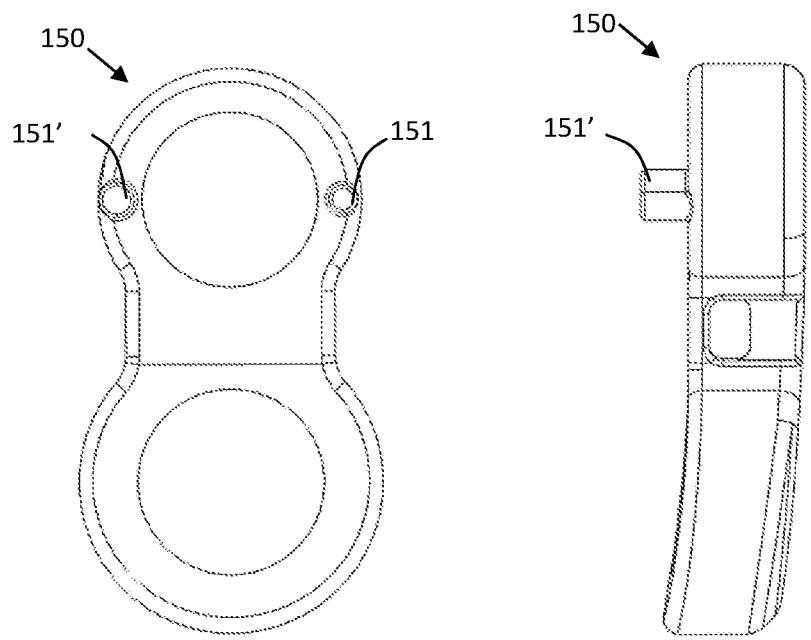
FIG. 22 shows a rear view of the fixation plate in accordance with the first embodiment, the fixation plate shown having at least one guide pin configured to mate with an expandable implant device.
FIG. 23 shows a side view of the fixation plate in accordance with the first embodiment.

The expandable implant device 100 may include one or more guide pin apertures (117, 117') to receive guide pins of a fixation plate (151, FIG. 22). A careful review of FIG. 16 and FIG. 22 will reveal that the this illustrated embodiment of an expandable implant device 100 includes a keyed design wherein three of the one or more guide pin apertures 117 of the first endplate are sized to receive a small guide pin (151, FIG. 22) of a keyed fixation plate. Likewise, three guide pin apertures 117' of the first endplate are sized to receive a large guide pin (151', FIG. 22) of the keyed fixation plate. This allows the surgeon to orient the fixation plate of the expandable implant device at various angles, as allowed by each of the three pairs of guide pin apertures while preventing the surgeon from installing the fixation plate upside-down. In this illustration the three guide pin apertures 117 to the left of the threaded aperture 140 are larger than the three guide pin apertures 117' to the right of the threaded aperture 140. In this embodiment the guide pin apertures 117, 117' are positioned radially around the threaded aperture 140, such that the distance from center of the threaded aperture 140 to each of the guide pin apertures is the same. As such, since the distance between the guide pins on the fixation plate is fixed, the fixation plate can only be mounted upon the expandable implant device in three possible orientations relative to the first endplate 110. These three orientations correspond to the three pairs of keyed guide pin apertures. The illustrated embodiment includes three pairs of keyed apertures, as one with skill in the art may appreciate any number or size of guide pins and guide pin apertures may be chosen while utilizing this keyed function.

Figure 17:
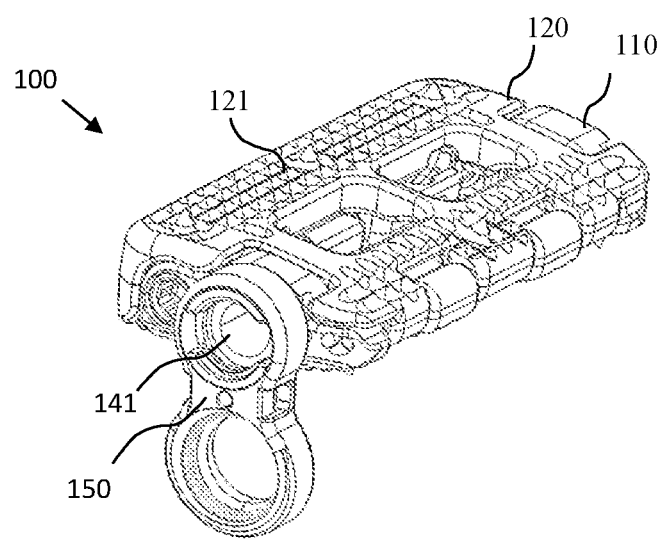
FIG. 17 shows a perspective view of the expandable implant device in accordance with the first embodiment, the expandable implant device coupled to a fixation plate via a set-screw.

FIG. 17 shows a perspective view of the expandable implant device 100 coupled to an embodiment of a fixation plate 150 via a set-screw 141. The fixation plate 150 is configured to be to be utilized as an anti-migration feature, to secure the expandable implant device 100 with respect to a patient's bone, via a bone fixation element.

Figure 18:
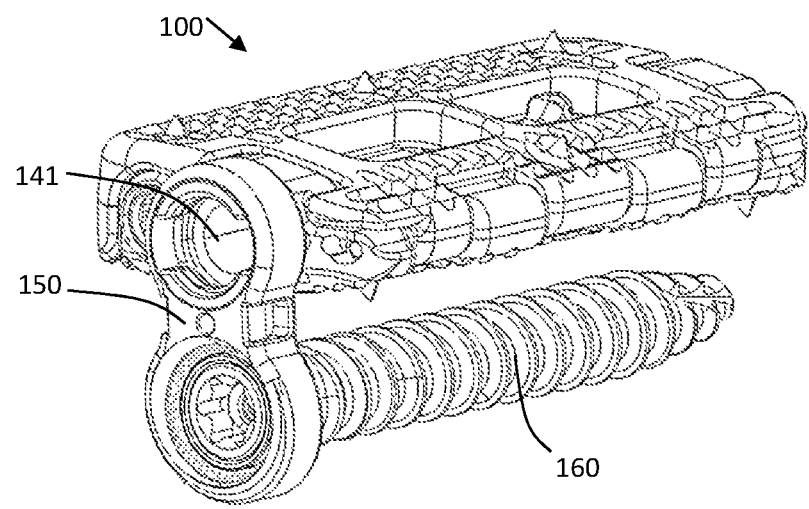
FIG. 18 shows a perspective view of the expandable implant device in accordance with the first embodiment, the expandable implant device coupled to a fixation plate, wherein the fixation plate is also configured to receive a bone screw therethrough.

FIG. 18 shows the expandable implant device 100 in accordance with the first embodiment, the expandable implant device is shown coupled to a fixation plate 150, with the fixation plate 150 coupled to a bone screw 155. The fixation element, here a bone screw 155 helps secure the expandable implant device in place, and prevent slippage.

Figure 19:
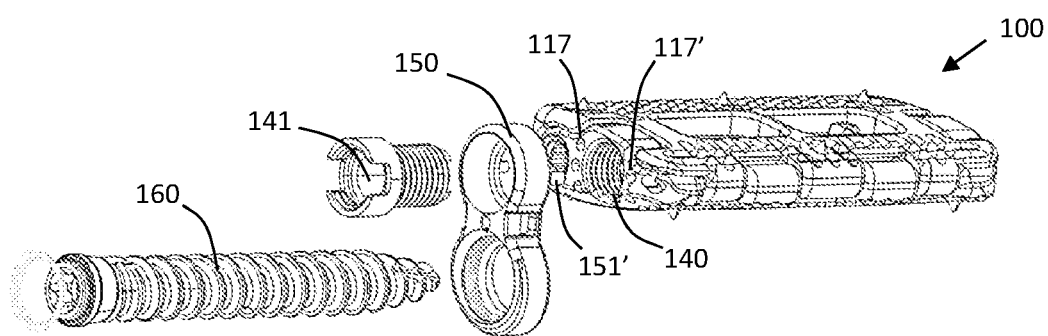
FIG. 19 shows an exploded view of the expandable implant device in accordance with the first embodiment, with the fixation plate shown decoupled from the expandable implant device.

FIG. 19 shows an exploded view of an expandable implant device 100 decoupled from a fixation plate 150, and a bone screw 155. After placement of the expandable implant device 100, a fixation plate 150 may be coupled to the expandable implant device 100 via a set screw 141. A fixation device, such as a bone screw 155 may then be used to secure the expandable implant device 100 within the intervertebral space and help prevent slippage of the expandable implant device.

Figures 20, 21:
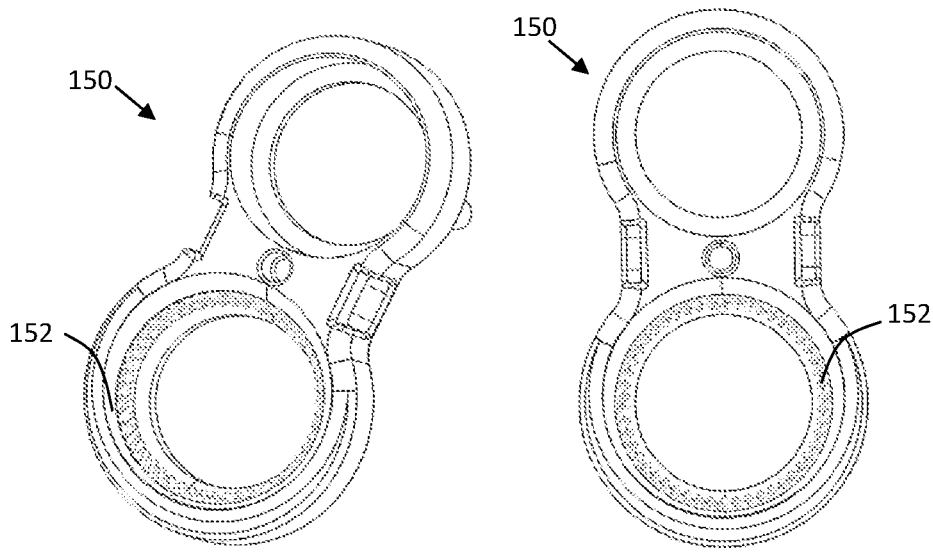
FIG. 20 shows a perspective view of a fixation plate in accordance with a first embodiment.
FIG. 21 shows a front view of the fixation plate in accordance with the first embodiment.

FIGS. 20-23 show various views of one embodiment of a fixation plate 150. FIG. 20 shows a perspective view of a fixation plate 150, the fixation plate 150 including two apertures one for receiving a set screw to secure the fixation plate 150 to an expandable implant device 100. The aperture dimensioned to receive a bone screw is shown including a canted coil mechanism 152. FIG. 21 shows a front view of a fixation plate 150 the fixation plate 150 shown including inserter mating apertures. FIG. 22 shows a rear view of a fixation plate 150, the fixation plate 150 shown having two guide pins 151 configured to mate with an expandable implant device. In this embodiment the fixation plate 150 is keyed, with one large guide pin 151' and one small guide pin 151. FIG. 23 shows a side view of a fixation plate 150.

The fixation plate 150 is shown including a canted coil mechanism 152 as an anti-back-out feature, but other types may be used to secure the implant position with respect to adjacent bone once it is placed and sized. For example some embodiments may include a polymeric member for ultrasonic welding.

Additionally, methods of use are provided for the expandable implant device 100. Some methods include the steps of: accessing a disc space via a lateral or an anterior approach; Preparing the disc space; inserting the expandable implant device into the prepared disc space in a closed configuration having an initial lordosis angle; rotating a drive screw of the expandable implant device using an adjustment tool, thereby causing an actuation of the expandable implant device to change the lordosis angle until a desired lordosis angle is achieved; removing the adjustment tool from the expandable implant device; packing the expandable implant device with bone graft or bone graft substitute through the threaded aperture on a proximal end of the inserted expandable implant device and/or packing bone graft or bone graft substitute around the expandable implant device within the disc space; attaching a fixation plate to a trailing end of the expandable implant device; and securing the fixation plate to a bone of the user to prevent slippage of the device to help assist the fusion process. It is contemplated that the methods of use may further include packing bone graft or bone graft substitute material into the fusion apertures of the device before insertion of the device into the disc space. It is also contemplated the step of attaching a fixation plate to the trailing end of the expandable device may occur before or after the device is implanted into the disc space, as well as before or after the device is adjusted from its initial lordosis angle to its desired lordosis angle.

The individual pieces of the expandable implant may be manufactured from titanium or any material commonly used to manufacture a surgical implant. Depending on the material chosen known fabrication methods may be utilized. For example, metal and/or thermoplastic components may be 3D printed, blow molded, or injection molded.

It is contemplated that in some embodiments at least a portion of the implant may be constructed out of a PEEK or porous PEEK material. It may be desirable to have a porous peek surface define the bone engagement surface 121 of one or more of the first endplate 110 and the second endplate 120. This porous bone contact surface may encourage bone ingrowth or ongrowth to the bone engagement surfaces of the endplates, as well as to act as an anti-migration feature.

Assembly instructions may include:

Placing a right threaded nut in proper orientation in first endplate with open end facing laterally. Threading the right bolt through lateral hole in first endplate into right threaded nut until medial ends of the bolt and threaded nut are flush.

Align spline lobed features with spring end (often called a nub) on leaf spring, and slide spline through leaf spring, while ensuring no permanent deformation occurs with leaf spring.

Place left threaded nut into first endplate with open end facing laterally. Thread left bolt through first endplate and through left threaded nut until left bolt threads are flush with inside of left nut as shown. Ensure both medial bolt surfaces are aligned with medial faces of nuts before pressing. This will ensure the expandable implant device will expand in a uniform fashion. Press both bolts together until medial faces are just touching central support strut in first endplate. Snap E-clips into grooves on drive screws. Rotate drive screw until threaded nuts are fully separated. Stick right linkage feet into mating slot feature on right threaded nut, with pull down pin oriented toward the posterior of the expandable implant device. Orient second endplate about sixty degrees relative to first endplate to allow right linkage pull down pin to slide into mating slot on second endplate. Keep right side of assembly together to prevent linkage from coming loose, and use, for example, tweezers to slide pull down pin on left linkage into second endplate pull down slot and align left linkage feet into mating slot in left threaded nut. Ensure that both linkages are fully seated in mating threaded nuts, and align pin holes of static and second endplate. Rotate drive screw to bring implant into the first or fully collapsed configuration. To join the first end of the second endplate to the first end of the first endplate press a hinge pin through hinge holes of static and second endplates until centered.

What is claimed is:

1. An expandable implant device comprising:
    a first endplate having a bone contacting surface and an opposite interior surface, a first side and a second side, and having a leading end and a trailing end, each of the leading end and the trailing end including an aperture in communication with an inner volume of the implant;
    a second endplate having bone contacting surface and an opposite interior surface, a first side and a second side, wherein the first side of the first endplate is hingedly coupled to the first side of the second endplate;
    an expansion mechanism disposed between the interior surface of the first endplate and the interior surface of the second endplate, the expansion mechanism including
        a drive screw extending across the entire length of the expandable implant device from the leading end of the first endplate to the trailing end of the first endplate and including a first threaded shank and a second threaded shank, and
        a first threaded nut configured to engage at least a portion of the first threaded shank and a second threaded nut configured to engage at least a portion of the second threaded shank; and
    at least one linkage coupled to the first threaded nut and extending from the first threaded nut to the inferior surface of the first endplate ad at least one linkage coupled to the second threaded nut and extending from the second threaded nut to the inferior surface of the first endplate,
    wherein the expandable implant device, including the expansion mechanism, is symmetrical about a central plane bisecting the leading end and the trailing end of the first endplate such that the expandable implant device has a first half that is a mirror image of a second half of the expandable implant device.

2. The expandable implant device of claim 1 wherein the expansion mechanism is disposed adjacent to the second sides of first and second endplates, wherein the second sides of the first and second endplates are opposite the first side.

3. The expandable implant device of claim 1 wherein at least one of the first endplate or the second endplate includes a planar extension extending perpendicularly to the bone contacting surface of the at least one of the first endplate or second endplate.

4. The expandable implant device of claim 3 wherein the planar extension is configured to enclose an inner volume of the expandable implant device.

5. The expandable implant device of claim 4 wherein at least one of the first endplate or the second endplate further comprise at least one fusion aperture extending from the bone contacting surface of at least one of the first endplate or the second endplate into the inner volume of the expandable implant device.

6. The expandable implant device of claim 1 further comprising a locking mechanism; wherein the locking mechanism is configured to prevent an undesired rotation of the drive screw.

7. The expandable implant device of claim 6 wherein the drive screw further comprises
a spline configured to couple the first threaded shank and the second threaded shank.

8. The expandable implant device of claim 7, wherein the locking mechanism further comprises a spring configured to engage the spline.

9. The expandable implant device of claim 1 wherein the first threaded shank has a right-handed thread pattern and the second threaded shank has a left-handed thread pattern.

10. The expandable implant device of claim 9 further comprising a second threaded nut coupled to a second linkage and configured to engage at least a portion of the second threaded shank.

11. The expandable implant device of claim 1, wherein the drive screw is configured to be actuated at the leading end or at the trailing end of the first endplate.

12. The expandable implant device of claim 1 wherein the aperture is a threaded aperture, the threaded aperture disposed on a proximal side of the implant device, the threaded aperture configured to receive at least a portion of a screw to secure a plate to the implant device.

13. The expandable implant device of claim 12 wherein the plate is a fixation plate dimensioned to receive a bone screw.

14. The expandable implant device of claim 13, wherein the trailing end of the first endplate is configured to receive the fixation plate in one of a plurality of positions.

15. The expandable implant device of claim 13, wherein the screw is a set screw.

* * * * *

UNITED STATES PATENT AND TRADEMARK OFFICE
CERTIFICATE OF CORRECTION

PATENT NO. : 11,273,047 B2
APPLICATION NO. : 16/224582
DATED : March 15, 2022
INVENTOR(S) : Christopher Besaw and Thomas Sweeney, III It is certified that error appears in the above-identified patent and that said Letters Patent is hereby corrected as shown below:

In the Claims

Column 12, In Claim 1, Line 53, "...surface of the first endplate ad at least one linkage..." is replaced with "surface of the first endplate and at least one linkage..."

Signed and Sealed this
Thirty-first Day of May, 2022

Katherine Kelly Vidal
Director of the United States Patent and Trademark Office